US00PP31195P3

(12) United States Plant Patent
Pierron-Darbonne

(10) Patent No.: US PP31,195 P3
(45) Date of Patent: Dec. 10, 2019

(54) BLACKBERRY PLANT NAMED 'PLABLACK 1401'

(50) Latin Name: ***Rubus* subgenus *Eubatus* sect. *Morifieri* & *Ursini* and hybrids**
Varietal Denomination: Plablack 1401

(71) Applicant: Plantas de Navarra, S.A. Sociedad Unipersonal, Navarra (ES)

(72) Inventor: Alexandre Pierron-Darbonne, Pamplona (ES)

(73) Assignee: Plantas de Navarra, S.A. Sociedad Unipersonal (ES)

( * ) Notice: Subject to any disclaimer, the term of this patent is extended or adjusted under 35 U.S.C. 154(b) by 0 days.

(21) Appl. No.: 15/998,296

(22) Filed: Aug. 1, 2018

(65) Prior Publication Data

US 2019/0045684 P1 Feb. 7, 2019

(30) Foreign Application Priority Data

Aug. 2, 2017 (QZ) ..... PBR 2017/1911

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./156, 203
See application file for complete search history.

*Primary Examiner* — Susan McCormick Ewoldt
*Assistant Examiner* — Karen M Redden
(74) *Attorney, Agent, or Firm* — Knobbe, Martens, Olson & Bear, LLP

(57) ABSTRACT

A new and distinct blackberry variety 'Plablack 1401' is characterized by a combination of traits which include, but are not limited to, weak anthocyanin coloration of dormant cane, many spines density, and abundant production of oblong shaped, and medium fruit size, a primocane fruiting habit that produces and maintains a strong vigorous plant with consistent fruit production on primocanes.

22 Drawing Sheets

Botanical classification: *Rubus* subgenus *Eubatus* sect. *Morifieri* & *Ursini* and hybrids.

Variety denomination: The new plant has the varietal denomination 'Plablack 1401'.

CROSS-REFERENCE TO RELATED APPLICATIONS

This application claims the benefit of European Community Plant Variety Office Application No. 2017/1911, for a blackberry variety named 'Plablack 1401', filed on Aug. 2, 2017, the entirety of which is incorporated by reference herein.

BACKGROUND

Disclosed herein is a new and distinct blackberry variety. The varietal denomination of the new variety is 'Plablack 1401'. The new variety was designated by the breeder as '14.01R.28'. The new variety of blackberry was created in a breeding program by crossing as seed parent an undistributed blackberry parent designated '13.01R.153' (unpatented) and as pollen parent an undistributed blackberry parent designated '10.04.05' (unpatented). Both the female and male parents are selections from the Applicant breeder's program. Both parental varieties are property of the Applicant and have not been commercialized. The Applicant maintains them in their nurseries, and both parental cultivars have never been commercialized.

The resulting seedling of the new variety was grown and asexually propagated by root cuttings in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY

The present invention relates to a new and distinct blackberry variety. The varietal denomination of the new variety is 'Plablack 1401'. New variety shows a primocane fruiting habit, produces and maintains a strong vigorous plant with consistent fruit production from middle September through the end of December on primocanes and in the ensuing year from the end of April through the beginning of June.

Among the characteristics which appear to distinguish the new variety from other varieties are a combination of traits which include weak anthocyanin coloration of dormant cane, many spines density, and abundant production of oblong shaped, and medium fruit size.

COMPARISON TO THE PARENTS

Neither the seed parental cultivar, '13.01R.153' nor the pollen parent cultivar, '10.04.05', has any patent or application for Plant Patent Rights in any country on the world. Both, seed and pollen parentals were obtained by the Applicant. They are selections from breeder's program of the Applicant. They are property of the Applicant. The Applicant maintains them in their nurseries, and both parental cultivars have never been commercialized.

The new variety is distinguished from its parents by the following characteristics possessed by 'Plablack 1401' which are different than, or not possessed, by the seed parent designated '13.01R.153' (unpatented) and the pollen parent designated '10.04.05' (unpatented).

The seed parent '13.01R.153' (unpatented) shows a spines density higher than the new variety 'Plablack 1401'.

The color of the petal in the flower of the seed parent '13.01R.153' (unpatented) is white, whereas the color of the petal in the flower of the new variety 'Plablack 1401' is pinkish (RHS white group color near 155 B to 155 A, with reddish pigmentation RHS red group near 55 D to 55 C).

The seed parent '13.01R.153' (unpatented) shows a longer fruit size than the new variety 'Plablack 1401'.

The pollen parent '10.04.05' (unpatented) shows a floricane fruiting habit, whereas the new variety 'Plablack 1401' shows a primocane fruiting habit.

The pollen parent '10.04.05' (unpatented) shows a smaller fruit size than the new variety 'Plablack 1401'.

The pollen parent '10.04.05' (unpatented) shows a medium ovate fruit shape, whereas the new variety 'Plablack 1401' shows an oblong fruit shape.

COMPARISON TO CLOSEST VARIETY

The new variety 'Plablack 1401' is closest to the variety 'Reuben' (patented in U.S. Plant Pat. No. 23,497) and to the variety 'Tupi' (unpatented), but is distinguished by the following characteristics possessed by 'Plablack 1401' which are different, or not possessed by, 'Reuben' (U.S. Plant Pat. No. 23,497) or 'Tupi' (unpatented).

'Reuben' (U.S. Plant Pat. No. 23,497) shows smaller spine density in canes than 'Plablack 1401'. Also, the spines of 'Reuben' (U.S. Plant Pat. No. 23,497) are shorter than 'Plablack 1401'.

'Reuben' (U.S. Plant Pat. No. 23,497) does not show spines in the petioles, whereas 'Plablack 1401' shows very few spines in the petioles.

The terminal leaflet of 'Reuben' (U.S. Plant Pat. No. 23,497) is moderately longer than broad, whereas the terminal leaflet of 'Plablack 1401' is much longer than broad.

The terminal leaflet of 'Reuben' U.S. Plant Patent No. (U.S. Plant Pat. No. 23,497) shows an acute shape of base, whereas the terminal leaflet of 'Plablack 1401' shows an acute to rounded shape of base.

'Reuben' (U.S. Plant Pat. No. 23,497) shows a white petal color (RHS white group color near 155 D to 155 C), whereas 'Plablack 1401' shows a white petal color (RHS white group color near 155 B to 155 A) with reddish pigmentation (RHS red group near 55 D to 55 C).

'Reuben' (U.S. Plant Pat. No. 23,497) maintains petals stuck to the fruits during the development and maturing of the fruits. 'Plablack 1401' does not present petals stuck to the fruits.

'Reuben' (U.S. Plant Pat. No. 23,497) shows a medium ovate shaped fruit and a medium fruit size, whereas 'Plablack 1401' shows an oblong shaped fruit and a bigger fruit size than 'Reuben' (U.S. Plant Pat. No. 23,497).

Time of beginning of flowering on current year's cane and time of beginning of fruit ripening on previous year's cane of 'Reuben' (U.S. Plant Pat. No. 23,497) is early, whereas in 'Plablack 1401' it is very early.

'Tupi' (unpatented) shows larger spines density in canes than 'Plablack 1401'.

'Tupi' (unpatented) shows larger number of spines in the petiole of leaves than 'Plablack 1401'.

'Tupi' (unpatented) shows an elliptic shaped fruit whereas 'Plablack 1401' shows an oblong shaped fruit.

Differences in the spine density in canes of 'Plablack 1401' (designated 14.01R.28) and 'Reuben' (U.S. Plant Pat. No. 23,497) are shown in FIG. 7, FIG. 8 and FIG. 16.

Differences in spine density in the petioles, ratio length/width of the terminal leaflet, and the shape of the base of terminal leaflet of 'Plablack 1401' (designated 14.01R.28) and 'Reuben' (U.S. Plant Pat. No. 23,497) are shown in FIG. 3 and FIG. 17.

Differences in the petal color of 'Plablack 1401' (designated 14.01R.28) and 'Reuben' (U.S. Plant Pat. No. 23,497) are shown in FIG. 9 and FIG. 18.

Differences in the maintenance of petals stuck to the fruits during the development and maturing of the fruits between 'Plablack 1401' (designated 14.01R.28) and 'Reuben' (U.S. Plant Pat. No. 23,497) are shown in FIG. 2 and FIG. 15.

Differences in fruit shape and fruit size of 'Plablack 1401' (designated 14.01R.28) and 'Reuben' (U.S. Plant Pat. No. 23,497) are shown in FIG. 13, FIG. 14 and FIG. 19.

Differences in the spines density in canes of 'Plablack 1401' (designated 14.01R.28) and 'Tupi' (unpatented) are shown in FIG. 7, FIG. 8 and FIG. 20.

Differences in spine density in the petioles of 'Plablack 1401' (designated 14.01R.28) and 'Tupi' (unpatented) are shown in FIG. 3 and FIG. 21.

Differences in fruit shape of 'Plablack 1401' (designated 14.01R.28) and 'Tupi' (unpatented) are shown in FIG. 13, FIG. 14 and FIG. 22.

BRIEF DESCRIPTION OF THE ILLUSTRATIONS

The accompanying photographs show typical specimens of the new variety, designated 14.01R.28 in the illustrations, including fruit, foliage and flower, in color as nearly true as it is reasonably possible to make in color illustrations of this character.

The plants depicted in the drawings were planted June 15 in Cartaya (Huelva), Spain, about 7° W, 37° N, 45 feet elevation.

Drawings/photographs were taken in December (about December 10 and December 30): minimum temperate about 5° to 6° Centigrade, maximum temperate about 16° to 20° Centigrade and May (about May 8 and May 16): minimum temperate about 13° to 15° Centigrade, maximum temperate about 26° to 29° Centigrade.

FIG. 1 and FIG. 2 show several plants of the new variety (designated 14.01R.28) which exhibit a upright habit plant.

FIG. 3 and FIG. 4 show the upperside and the underside, respectively, of a complete leaf of the new variety (designated 14.01R.28). In its we can see that the leaf color of upper side of the new variety (designated 14.01R.28) is a green color (RHS green group near 141 B to 141 A) and the leaf color of underside of the new variety (designated 14.01R.28) is RHS green group color (near 143 B to 143 A) and the petiole without spines.

FIG. 5 and FIG. 6 show the upperside and the underside, respectively, of terminal leaflet of the new variety (designated 14.01R.28). In it, we can see that the leaf color of the upper side of the new variety (designated 14.01R.28) is a green color (RHS green group near 141 B to 141 A) and the leaf color of underside of the new variety (designated 14.01R.28) is RHS green group color (near 143 B to 143 A) and the length of terminal leaflet in the new variety (designated 14.01R.28) is long.

FIG. 7 shows the color of young shoots of the new variety (designated 14.01R.28) RHS green group (near 139 C to 139 B), with a weak anthocyanin coloration during rapid growth (RHS greyed-red group near 180 C to 180 B), medium spine density, typical color at the bases of its spines (RHS red group color near 52 D to 52 B) and typical color at the tips of spines (RHS yellow-orange group color (near 19 D to 20 D).

Figure 1:
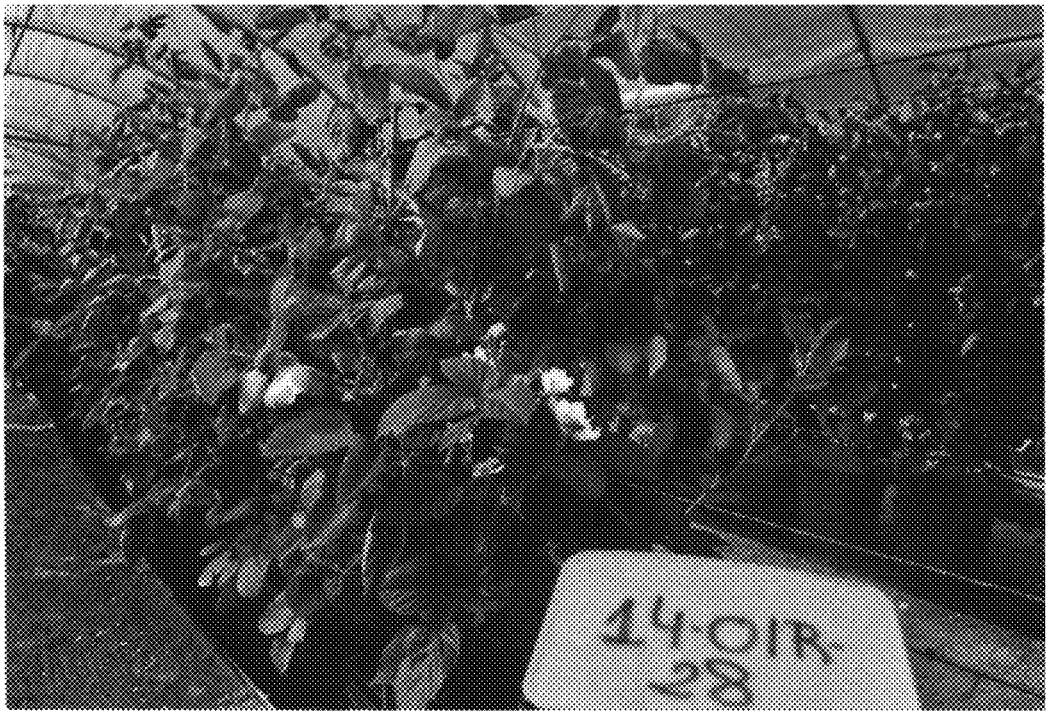
Figure 2:
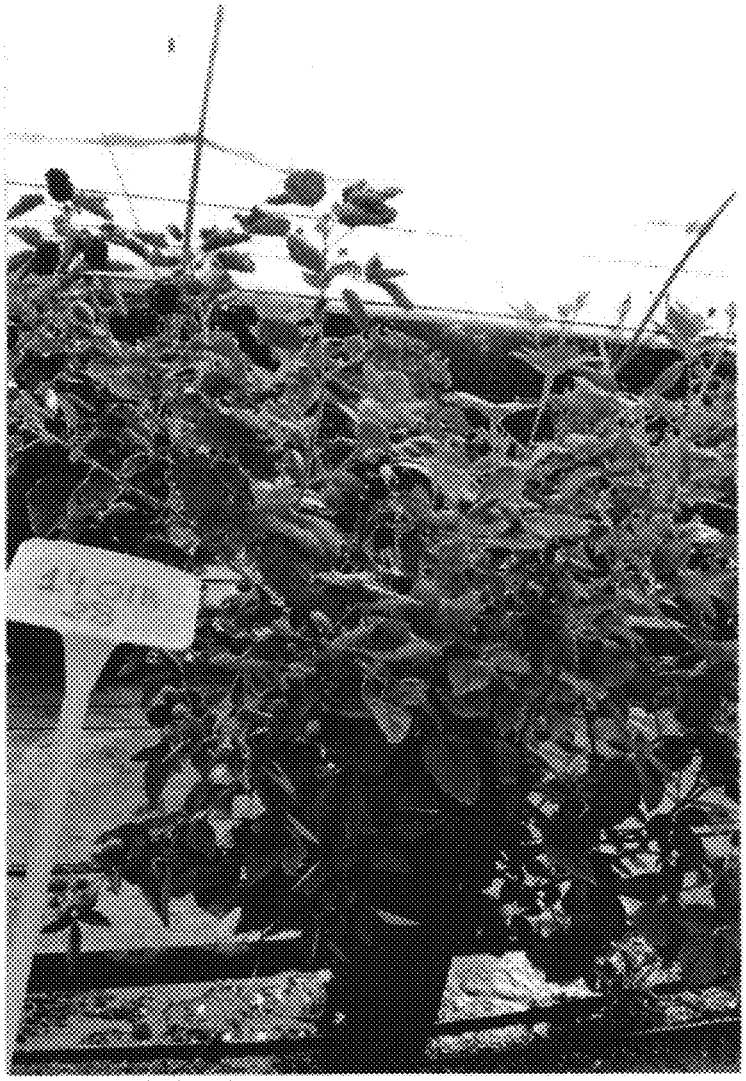
Figure 3:
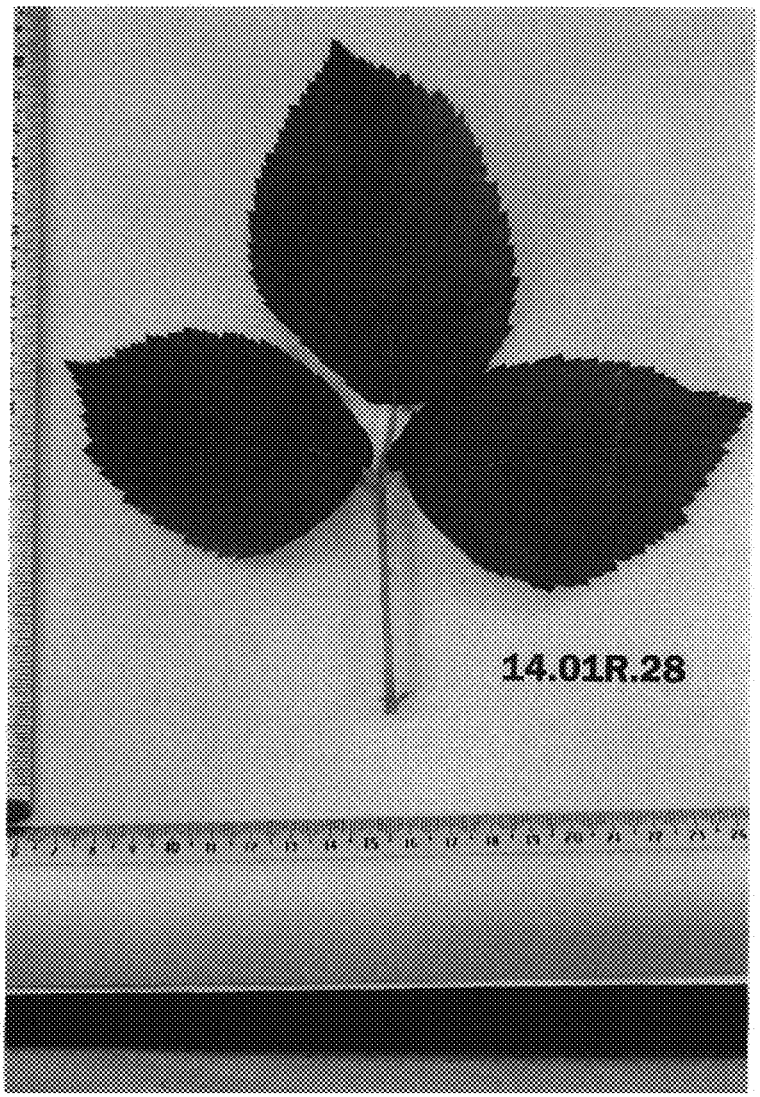
Figure 4:
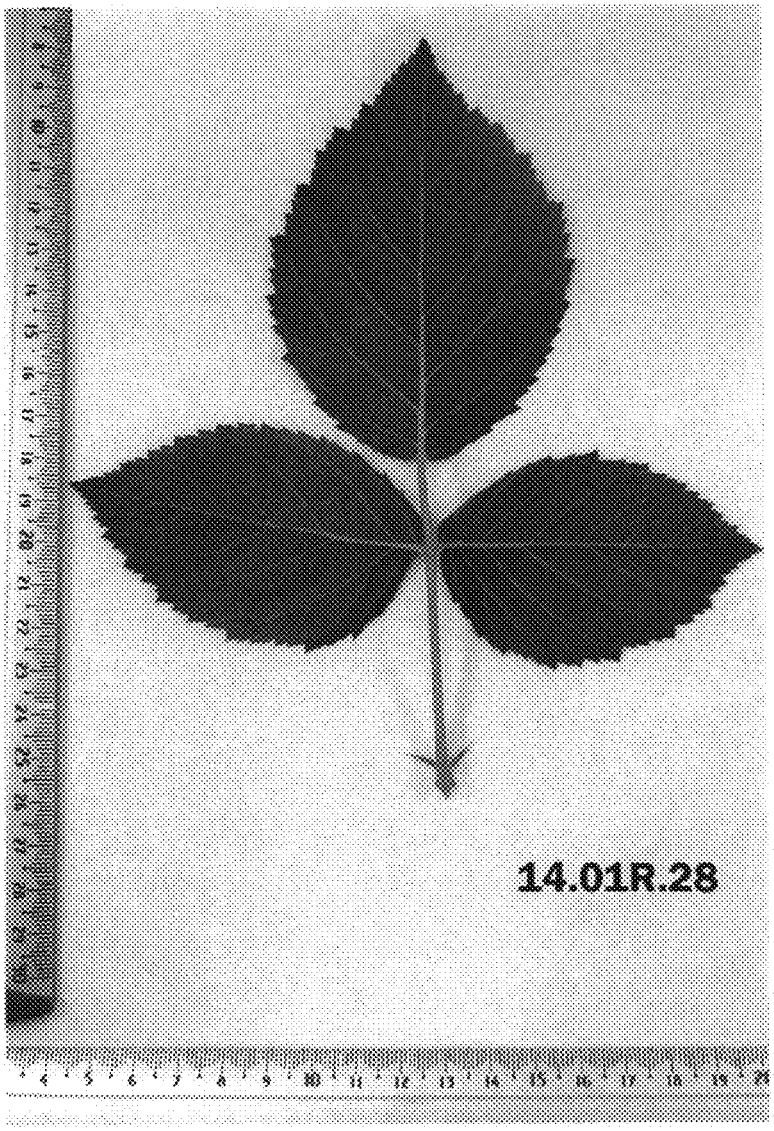
Figure 5:
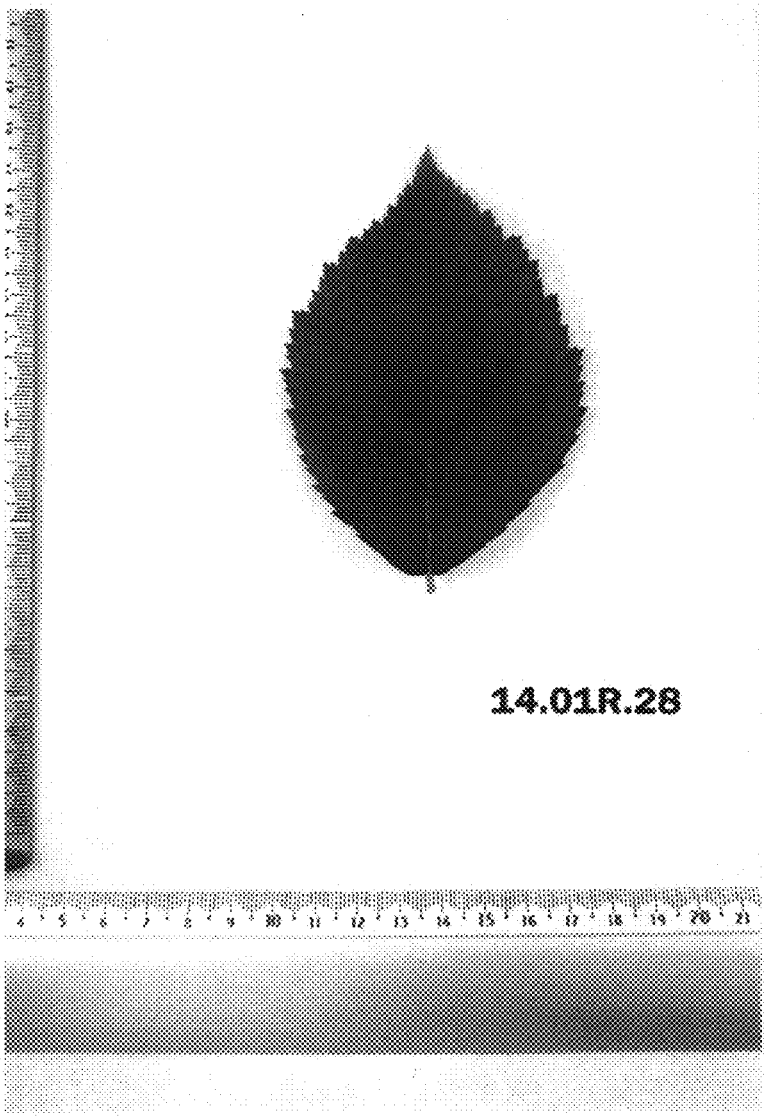
Figure 6:
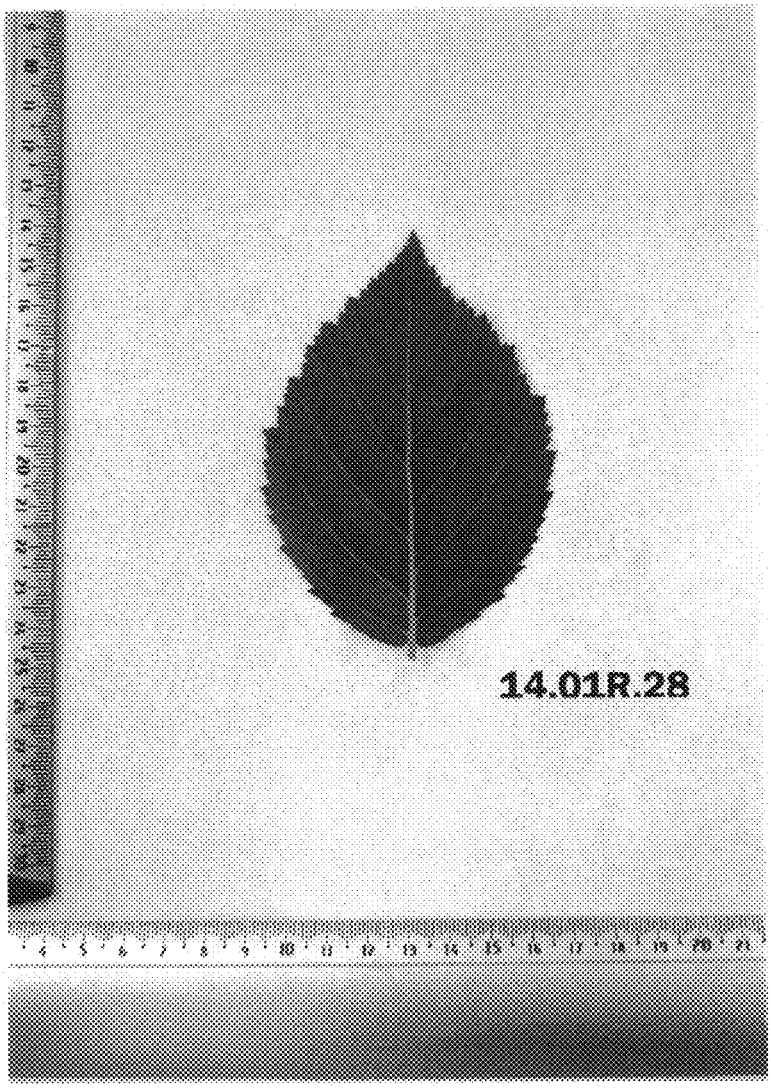
Figure 7:
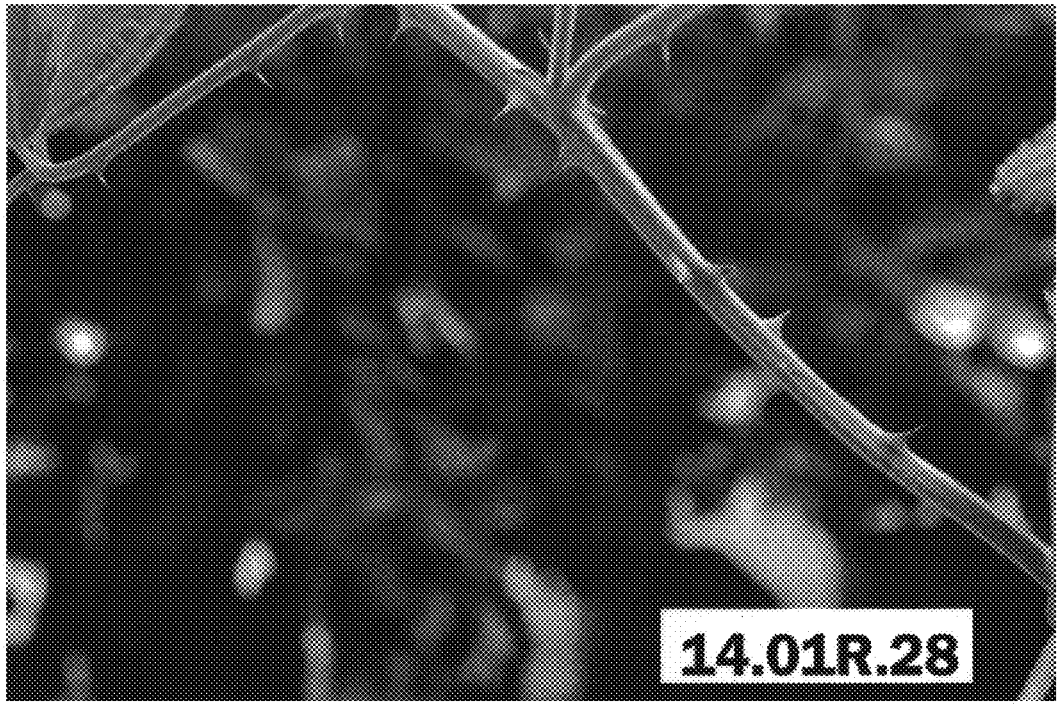
Figure 8:
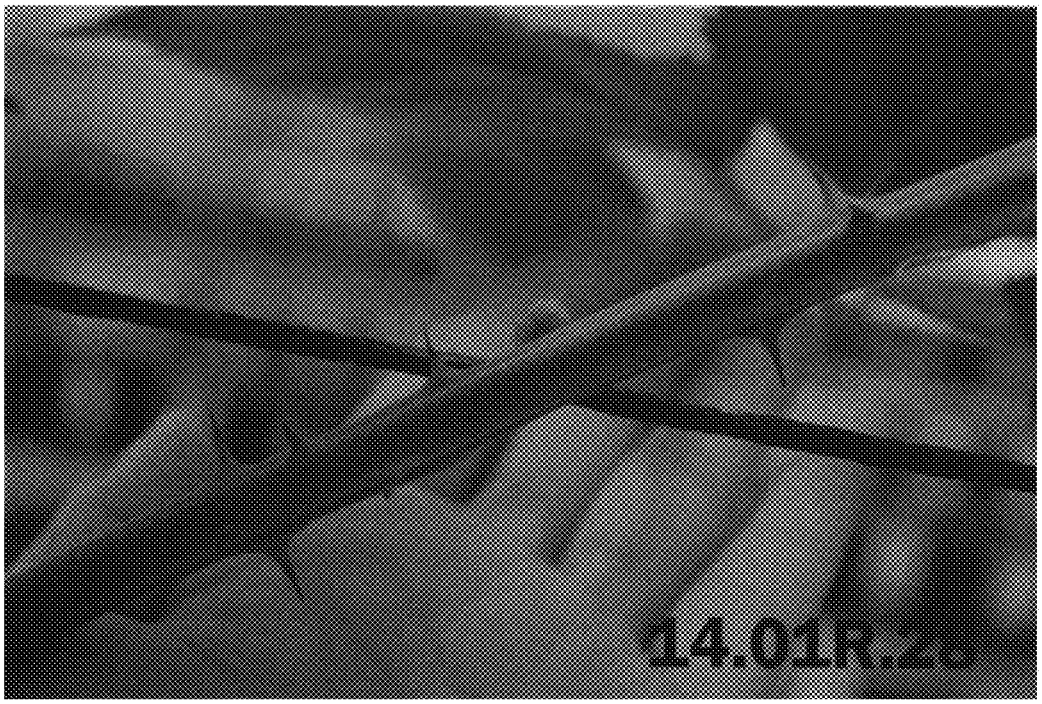
FIG. 8 shows the dormant cane with few pubescence downward, medium spines density, typical color at base of spines (RHS green group color near 138 D to 138 C) and typical color at tip of spines (RHS greyed-orange group color near 173 D to 173 A).
Figure 9:
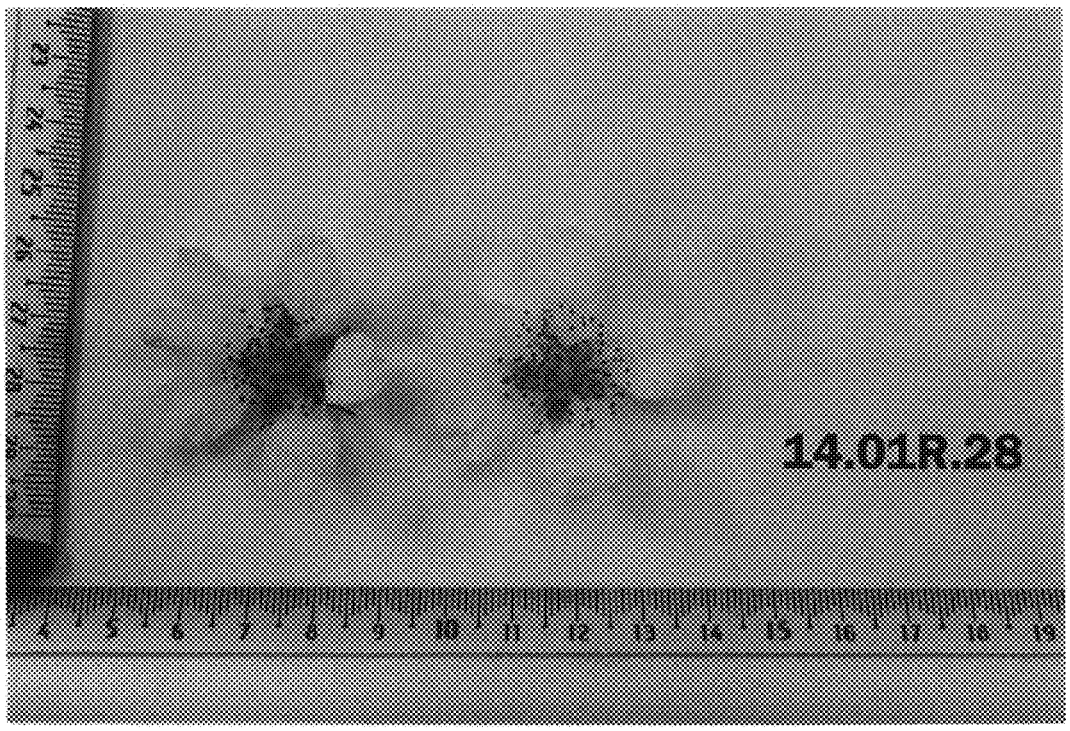
FIG. 9 shows typical flowers of the new variety (designated 14.01R.28).
Figure 10:
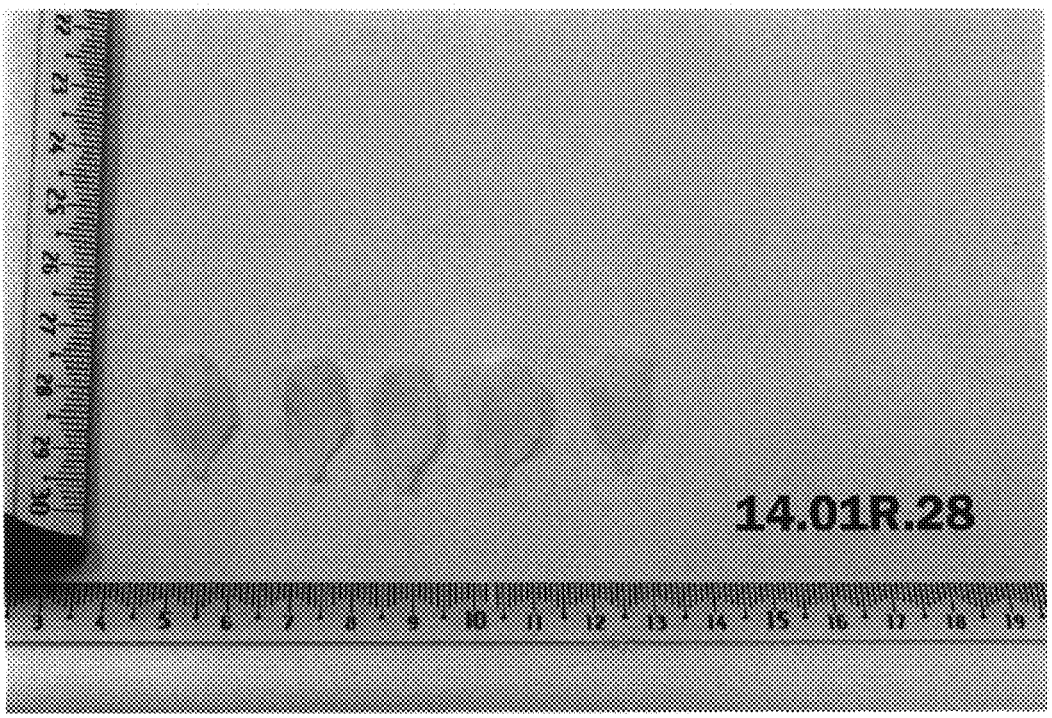

FIG. 10 shows typical petals of the new variety (designated 14.01R.28) with medium long flat elliptic shape and RHS white group color (near 155 B to 155 A) and reddish pigmentation RHS red group (near 55 D to 55 C).

Figure 11:
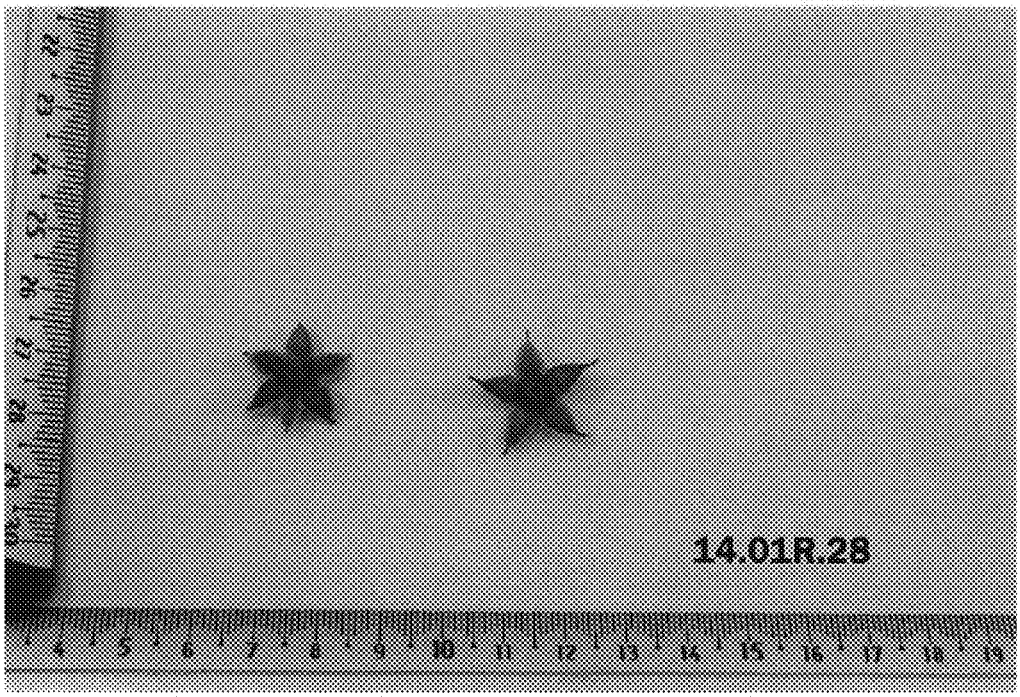

FIG. 11 shows typical sepals of the new variety (designated 14.01R.28) with triangular shape, acuminated apex and green color (RHS green group near 143 C to 143 A).

Figure 12:
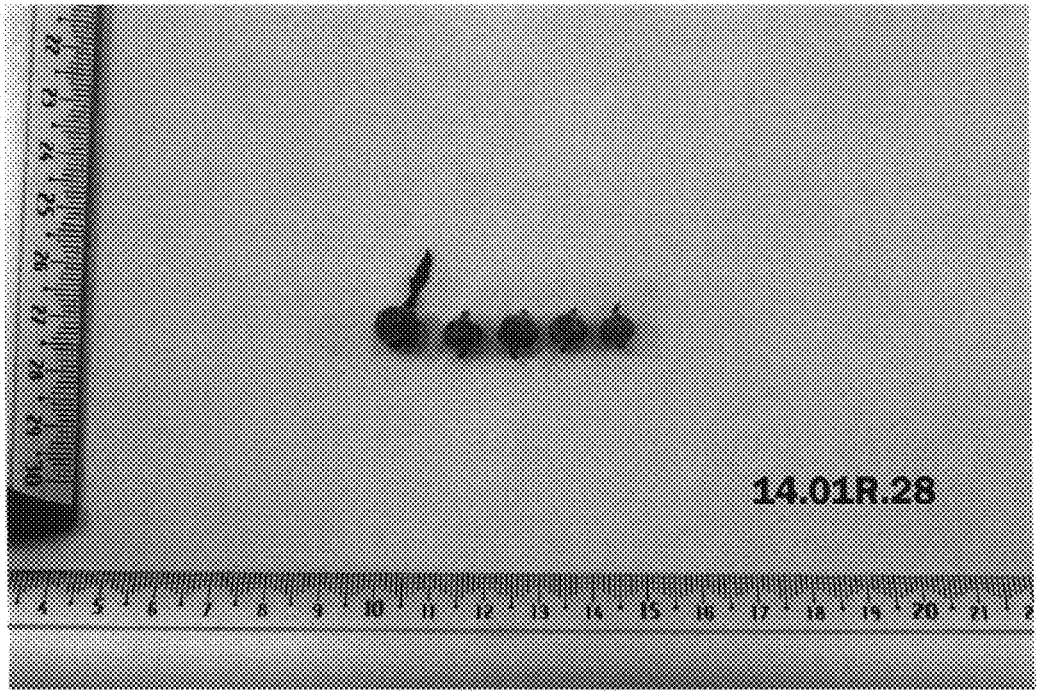

FIG. 12 shows typical flower buds of the new variety (designated 14.01R.28) with rounded shape and green color and green color (RHS green group near 143 B to 143 A).

Figure 13:
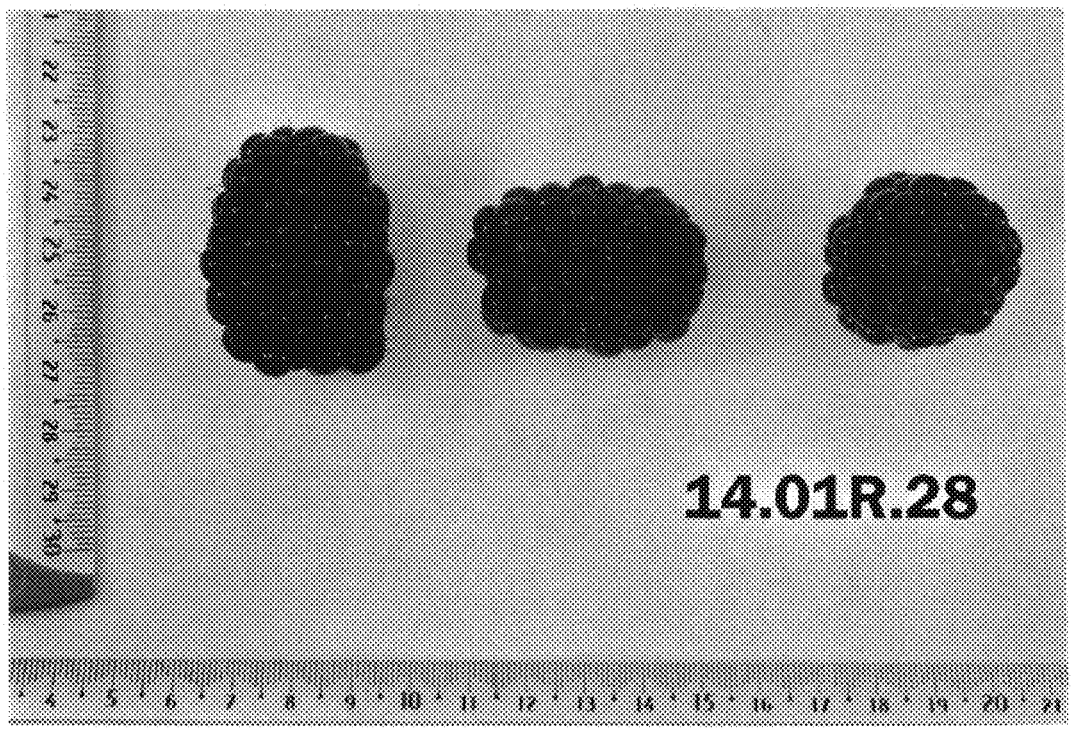
Figure 14:
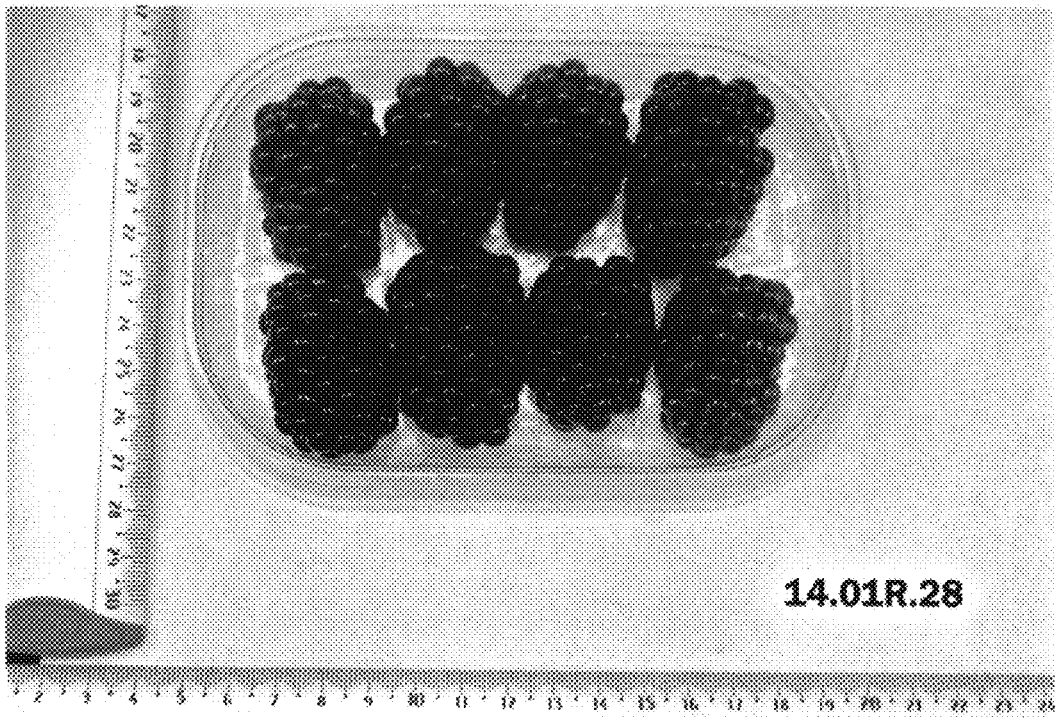

FIG. 13 and FIG. 14 show typical fruits of the new variety (designated 14.01R.28) with oblong shapes and black color (RHS black group near 202 A).

Figure 15:
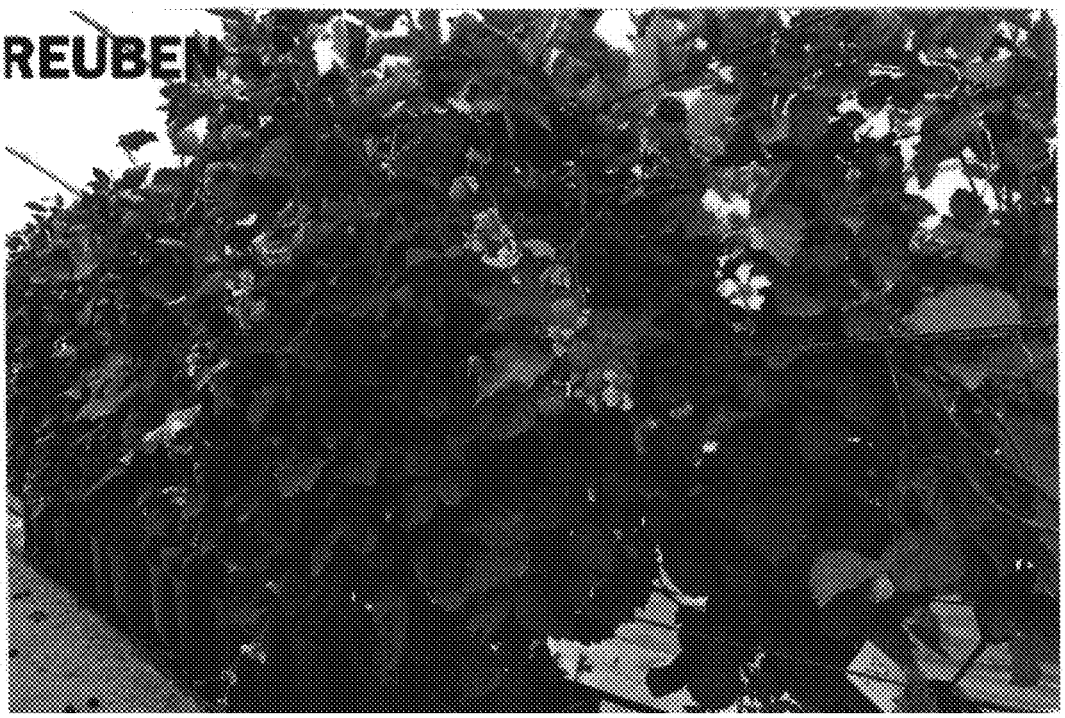

FIG. 15 shows several plants of 'Reuben' (U.S. Plant Pat. No. 23,497), which maintain petals stuck to the fruits during the development and maturing of the fruits.

Figure 16:
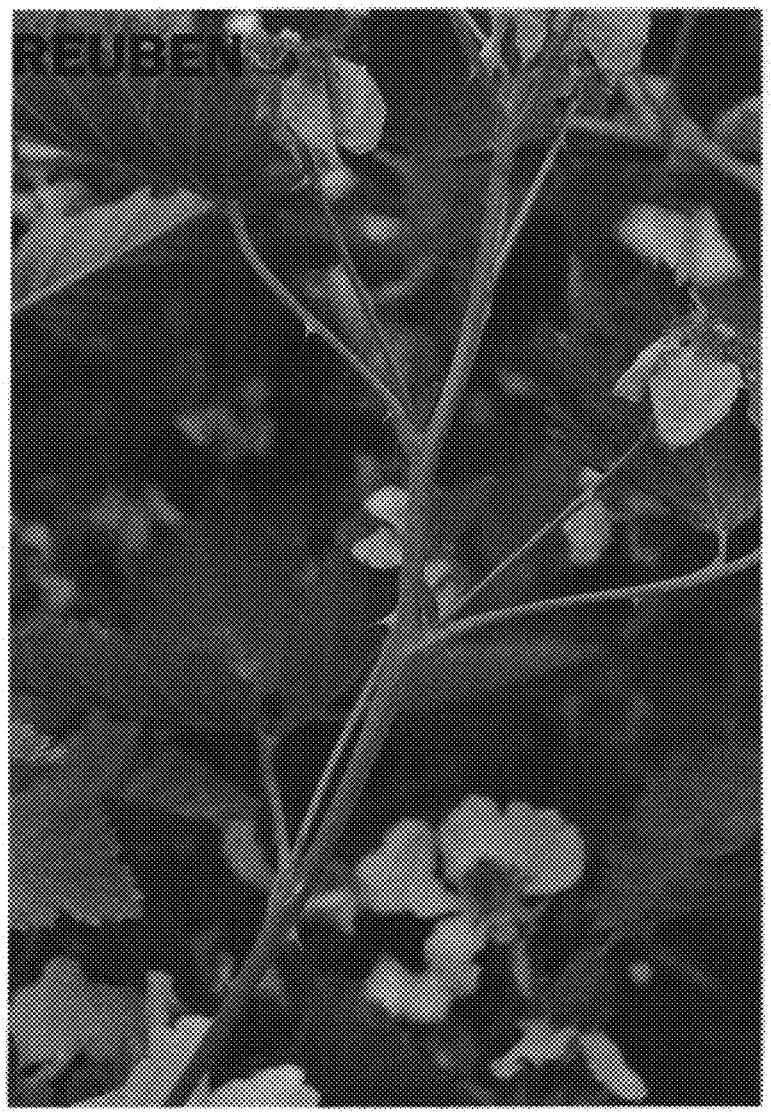

FIG. 16 shows the small spines density in canes of 'Reuben' (U.S. Plant Pat. No. 23,497).

Figure 17:
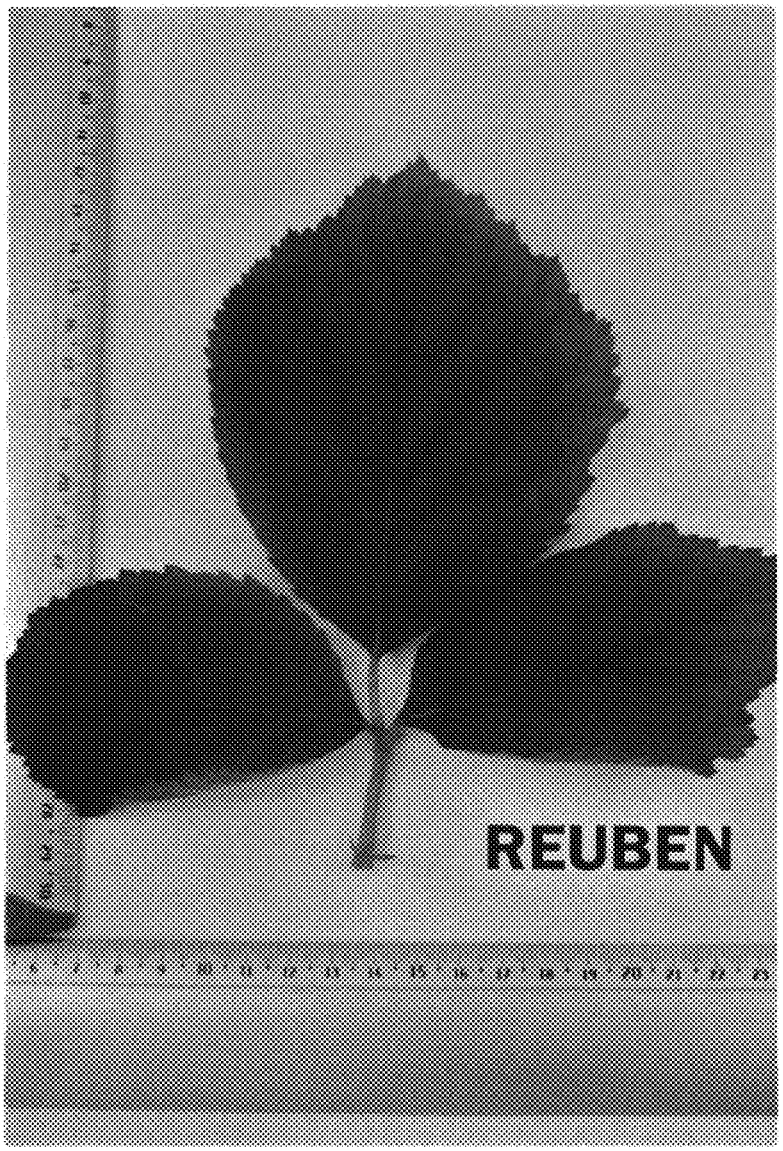

FIG. 17 shows a complete leaf of 'Reuben' (U.S. Plant Pat. No. 23,497). In it is appreciated that it does not show spines in the petiole, and the terminal leaflet is moderately longer than broad and shows an acute shape of the base.

Figure 18:
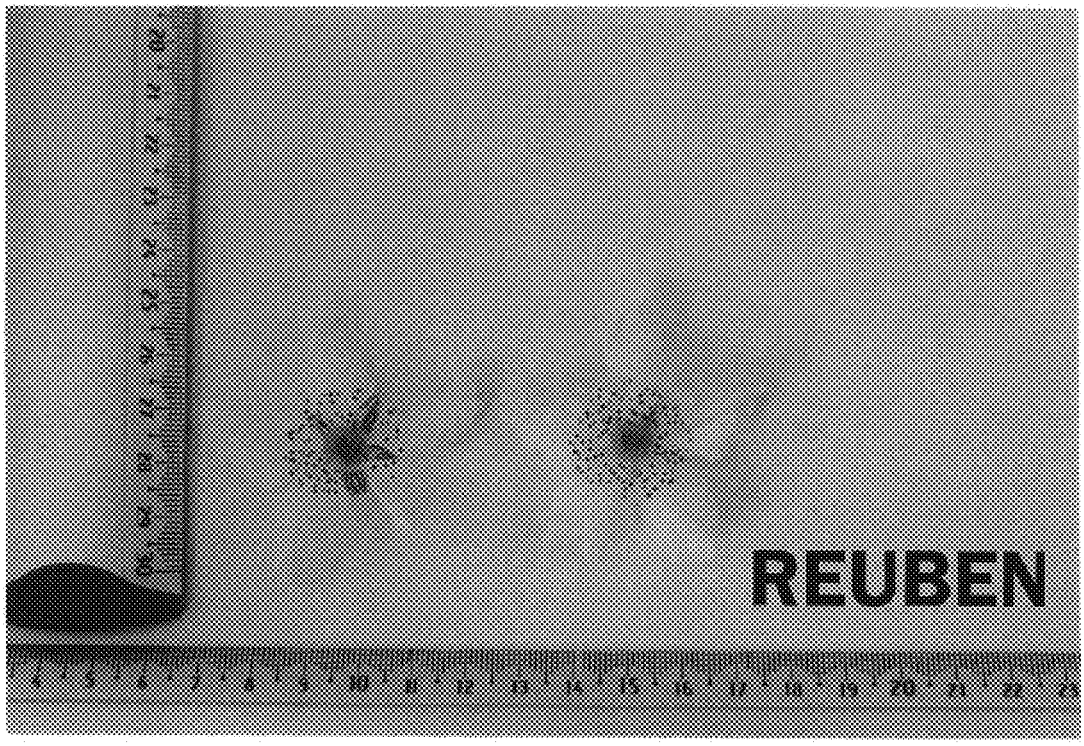

FIG. 18 shows typical flower of 'Reuben' (U.S. Plant Pat. No. 23,497) with a white petal color (RHS white group color near 155 D to 155 C).

Figure 19:
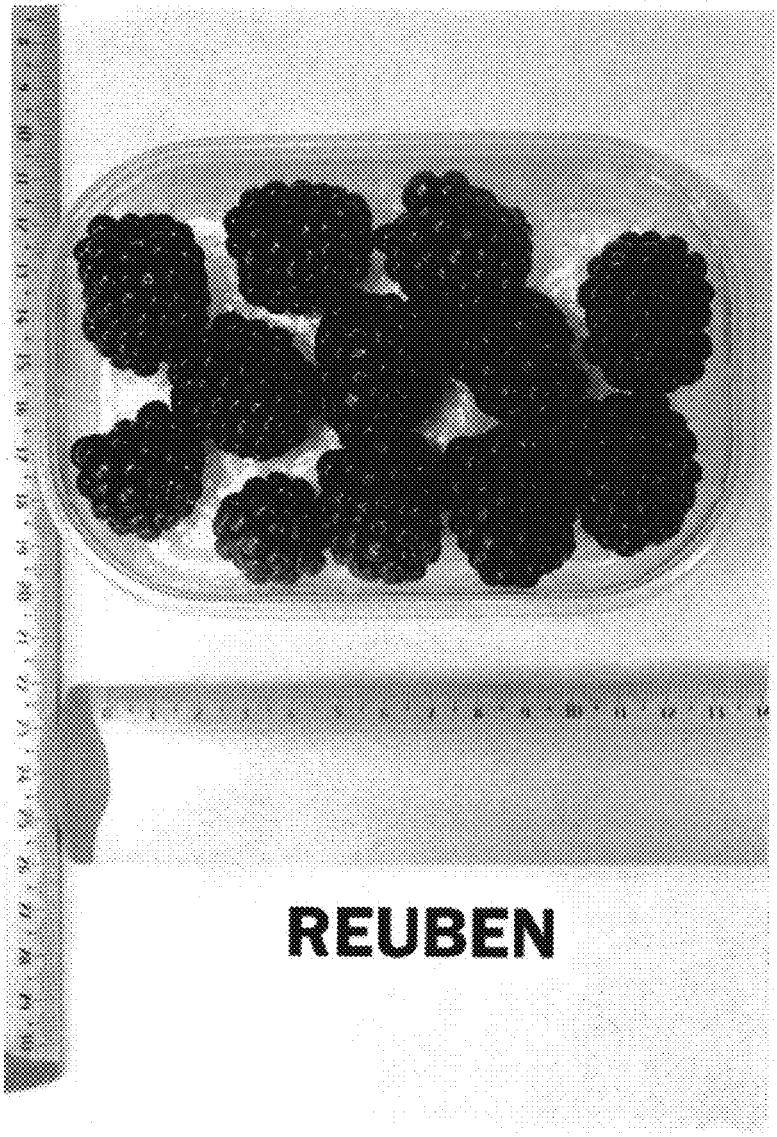

FIG. 19 shows typical fruits medium ovate shaped fruit and a medium fruit size of 'Reuben' (U.S. Plant Pat. No. 23,497).

Figure 20:
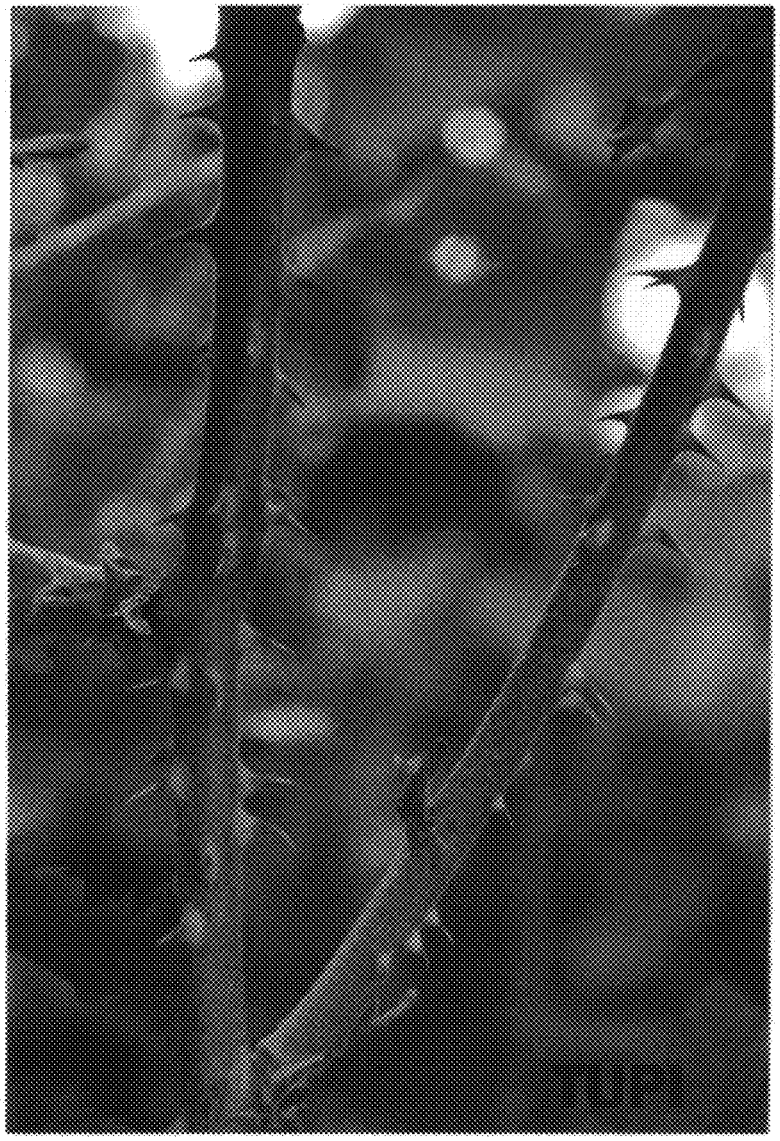

FIG. 20 shows a typical spine density in canes of 'Tupi' (unpatented).

Figure 21:
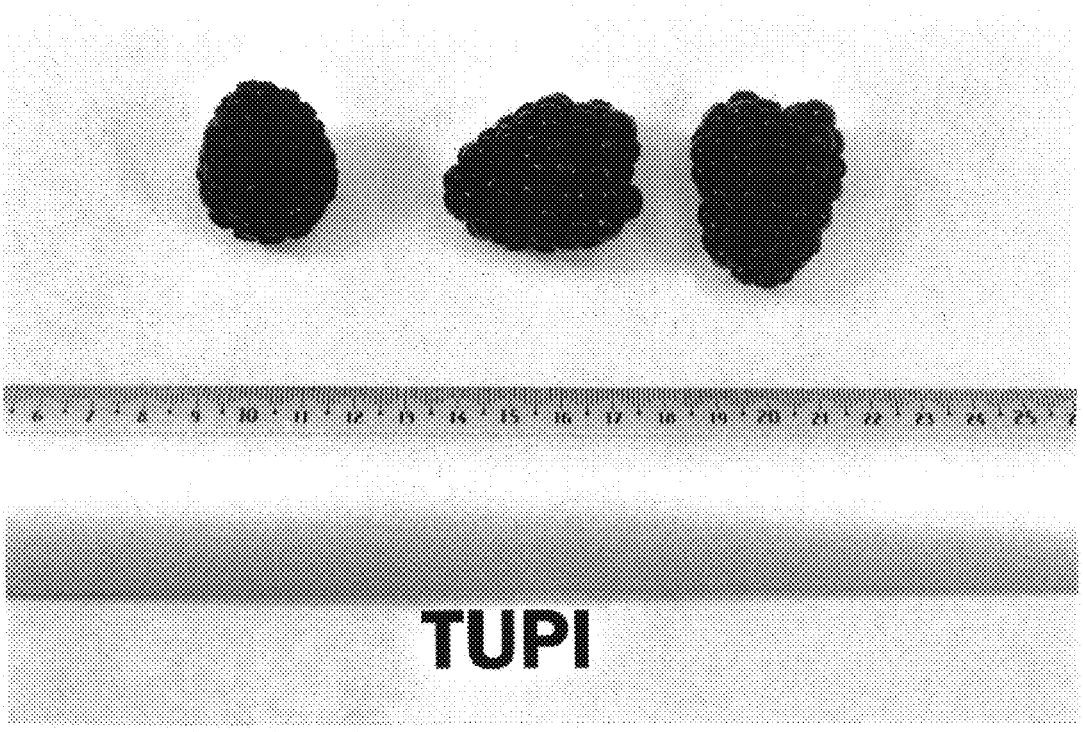

FIG. 21 shows the typical spine density in the petiole of a leaf of 'Tupi' (unpatented).

Figure 22:
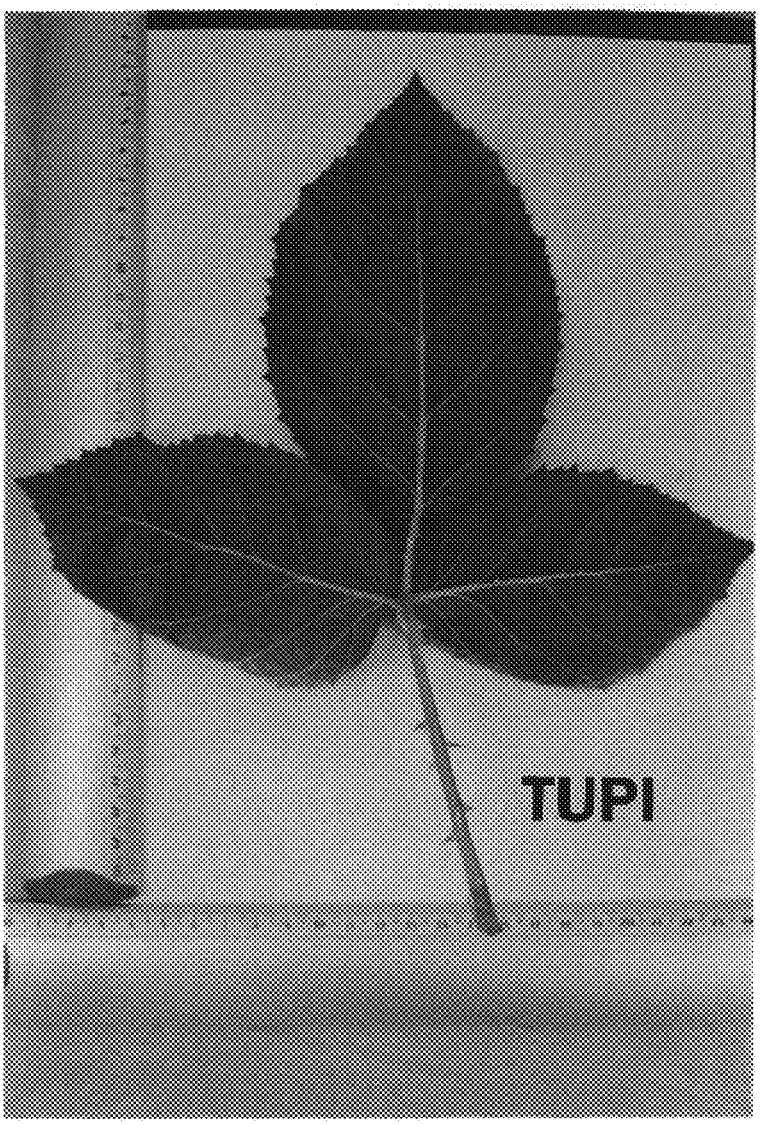

FIG. 22 shows typical fruits of 'Tupi' (unpatented) with elliptic shape.

DESCRIPTION OF THE NEW VARIETY

The following description is in accordance with UPOV terminology and the color terminology herein is in accordance with The Royal Horticultural Society Colour Chart (R.H.S.C.C.), 3rd edition published in 1995.

The color descriptions and other phenotypical descriptions may deviate from the stated values and descriptions depending upon variation in environmental, seasonal, climatic and cultural conditions.

Throughout this specification, color names beginning with a small letter signify that the name of that color, as used in common speech is aptly descriptive. Color names beginning with capital letter designate values based upon The R.H.S. Colour Chart published by The Royal Horticultural society, London, England, 1995.

The following detailed description of the new variety is based upon observations taken of plants and fruits grown "underglass," i.e., under tunnel, in Cartaya (Huelva), Spain, 7° W., 37° N., 45 feet elevation.

PROPAGATION

The new variety is principally propagated by way of root cuttings. Although propagation by root cuttings is presently preferred, other known methods of propagating blackberry plants may be used. Blackberries root and develop well after transplanting.

'Plablack 1401' is propagated by root cuttings. It is a primocane variety with fruit production from the middle of September through the end of December on primocanes and in the ensuing year from the end of April through the beginning of June. 'Plablack 1401' is a self-fertile variety. It produces large quantities of pollen throughout the seasons and pollination is good.

Plants described are from high elevation nursery in Segovia, Spain, 3° 59'W., 41° 22'N., 2742 feet elevation. Trials were pursued in in Cartaya (Huelva), Spain. Date of planting (two years) of the plants was June 14 in the first year and June 15 in the second year. Sample size was three repetitions (every year) with 100 plants per repetition (every year). The growing period in Huelva, Spain, where the observations on primocane production were made, is between about June 15 and June 2 of the following year. 'Plablack 1401' is a primocane variety, with consistent fruit production from middle September through ending December on primocanes and in the ensuing year from ending April through the beginning of June. After planting as aforesaid, plants are grown in raised beds under tunnel. Water and fertilizer were applied through drip irrigation.

GENERAL

TABLE 1

Table 1 shows the accumulated production of 1st Quality Fruit (g/plant).

| Variety | Middle in September and ending in December | Ending in April and beginning in June | Total |
|---|---|---|---|
| 'Plablack 1401' | 392.00 | 1300.00 | 1692.00 |
| 'Reuben' (U.S. Plant Pat. No. 23,497) | 94.10 | 1310.00 | 1404.10 |
| Tupi | — | 2127.00 | 2127.00 |

TABLE 2

Table 2 shows the accumulated total yield: 1st and 2nd Quality Fruit (g/plant).

| Variety | 1st + 2nd quality Middle in September and ending in December | 1st + 2nd quality Ending in September and beginning in June | Total |
|---|---|---|---|
| 'Plablack 1401' | 420.40 | 1475.00 | 1895.40 |
| 'Reuben' (U.S. Plant Pat. No. 23,497) | 166.10 | 1345.00 | 1511.10 |
| Tupi | — | 2201.00 | 2201.00 |

TABLE 3

Table 3 shows the production beginning in middle September and ending in December of First Quality Fruit (1st quality) and Second Quality Fruit (2nd quality) in g/plant.

| Variety | 1st Quality | 2nd Quality | TOTAL (1st Quality + 2nd Quality) | % 2nd Quality |
|---|---|---|---|---|
| 'Plablack 1401' | 392.00 | 28.40 | 420.40 | 6.75 |
| 'Reuben' (U.S. Plant Pat. No. 23,497) | 94.10 | 72.10 | 166.20 | 43.38 |
| 'Tupi' | — | — | — | — |

% 2nd Quality + (2nd Quality/TOTAL) × 100

TABLE 4

Table 4 shows the production beginning at the end of April and ending at the beginning of June of First Quality Fruit (1st quality) and Second Quality Fruit (2nd quality) in g/plant.

| Variety | 1st Quality | 2nd Quality | TOTAL (1st Quality +2nd Quality) | % 2nd Quality |
|---|---|---|---|---|
| 'Plablack 1401' | 1300.00 | 175.00 | 1475.00 | 11.86 |
| 'Reuben' (U.S. Plant Pat. No. 23,497) | 1310.00 | 35.00 | 1345.00 | 2.60 |
| 'Tupi' | 2127.00 | 74.00 | 2201.00 | 3.36 |

% 2nd Quality = (2nd Quality/TOTAL) × 100

TABLE 5

Table 5 shows Weight (g/Fruit) in two production periods: middle September to end December/end April to beginning June.

| Variety | Middle September to end December | End April to beginning June |
|---|---|---|
| 'Plablack 1401' | 11.5-13.6 | 14.5-16.4 |
| 'Reuben' (U.S. Plant Pat. No. 23,497) | 5.7-6.8 | 11.1-11.8 |
| 'Tupi' | 12.7-13.5 | |

WEIGHT is shown as the average weight per fruit (g/fruit) in First Quality Fruits.

TABLE 6

Table 6 shows a comparison of the fruit analysis between the new variety 'Plablack 1401' and its closest varieties 'Reuben' (U.S. Plant Pat. No. 23,497) and "Tupi".

FRUIT ANALYSIS

| | 'Plablack 1401' (14.01R.28) | 'Reuben' (U.S. Plant Pat. No. 23,497) | 'Tupi' |
|---|---|---|---|
| Firmness (Kg) | 0.30 | 0.40 | 0.30 |
| Humidity & Volatile Matter (%) | 87.90 | 86.10 | 87.30 |
| Dry Matter (%) | 12.10 | 13.90 | 12.70 |
| pH (to 20°) | 3.50 | 3.40 | 3.20 |
| Acidity as Anhydride Citric (%) | 0.58 | 0.89 | 0.86 |
| Soluble Solids (°Brix) | 10.60 | 10.70 | 9.30 |
| Maturity Index | 18.30 | 12.00 | 10.80 |
| Content in Ascorbic Acid (ppm) | 385.70 | 406.80 | 398.20 |
| Dominant Tonality (nm) | 515 | 515 | 510 |
| Luminosity: Transmittance tn 460 nm | 38.3 | 19.90 | 15.30 |

The following definitions apply:

Firmness refers to the fruit's resistance to penetration measured in Kilograms (Kg). The measure given has been obtained by the penetrometer ROZE Mod. Arbelette, with a 50 $mm^2$ section head.

Dry Matter refers to the residual weight left from the trituration of the fruit after the drying process at a temperature of 103° C.±2° C. until reaching constant weight. (%) Dry Matter=(Weight Dry Matter/Weight Fresh Matter)×100

Humidity & Volatile Matter represents the content in volatile matters and water of the fruits. (%) Humidity & Volatile Matter=100−% Dry Matter Maturity Index refers to the relation between Soluble solids and Acidity as Anhydride Citric.

Maturity Index=Soluble solids/Acidity as Anhydride Citric

DETAILED DESCRIPTION OF THE NEW VARIETY

The following additional information is provided to further describe the new variety:

Variety: 'Plablack 1401'

Breeder Ref: 14.01R.28

Classification: *Rubus* subgenus *Eubatus* sect. *Morifieri* & *Ursini* and hybrids.

Plants are growing in containers of 50 liters of capacity and they are described during cultivar's primocane.

Plant:

*Growth habit*.—Upright.

*Vigor*.—Strong.

*Cold tolerance*.—The new variety has not been grown in harsh winter conditions. It is expected to be of medium tolerance.

*Heat tolerance*.—The new variety has not been grown in harsh summer conditions It is expected to be of medium to high tolerance.

Dormant cane:

*Length*.—About 180 cm to 200 cm.

*Diameter*.—About 1.0 cm to 1.5 cm.

*Texture*.—Smooth.

*Internode length*.—About 5.0 cm to 7.0 cm.
*Pubescence*.—Few and downward.
*Anthocyanin coloration*.—Weak (RHS greyed-red group near 180 C to 180 B).
*Color*.—RHS green group (near 139 C to 139 B).

Young shoot:
*Length*.—About 170 cm to 180 cm.
*Diameter*.—About 0.7 cm to 0.9 cm.
*Texture*.—Smooth.
*Internode length*.—About 4.0 cm to 5.0 cm.
*Pubescence*.—Few and downward.
*Anthocyanin coloration during rapid growth*.—Absent or very weak (RHS greyed-red group near 180 D to 180 C).
*Color*.—RHS green group (near 139 C to 139 B).

Spines:
*Shape*.—Conical.
*Density*.—Medium.
*Number/cm*.—About 1 in to 2 in dormant canes and about 2 in to 3 in young shoots.
*Length*.—About 7.0 mm to 9.0 mm.
*Width*.—About 4.0 mm to 6.0 mm at the base.
*Apex*.—Straight.
*Texture*.—Rigid.
*Color at base in dormant cane*.—RHS green group color (near 138 D to 138 C).
*Color at tip in dormant cane*.—RHS greyed-orange group color (near 173 D to 173 A).
*Color at base in young shoot*.—RHS red group color (near 52 D to 52 B).
*Color at tip in young shoot*.—RHS yellow-orange group color (near 19 D to 20 D).
*Attitude of apex in relation to cane*.—Downwards.

Leaf:
*Type*.—Odd-pinnate.
*Number of leaflets*.—3.
*Arrangement of lateral leaflets*.—Free.
*Overlapping of lateral leaflets with terminal leaflet*.—Free.
*Upperside*.—RHS green group (near 141 B to 141 A).
*Underside*.—RHS green group color (near 143 B to 143 A).
*Length*.—17.5 cm to 18.5 cm.
*Width*.—About 15.5 cm to 16.5 cm.
*Profile of leaflets in cross section*.—V-shaped.
*Relief between veins*.—Medium.
*Upperside glossinesss*.—Strong.

Lateral leaflet:
*Shape*.—Elliptic.
*Length*.—About 8.0 cm to 9.0 cm.
*Width*.—About 4.5 cm to 5.0 cm.
*Shape of tip*.—Acuminate.
*Shape of base*.—Acute to rounded.
*Shape of margin*.—Bi-serrate.
*Upperside rugosity*.—Medium.
*Underside texture*.—Medium.
*Upperside*.—RHS green group (near 141 B to 141 A).
*Underside*.—RHS green group color (near 143 B to 143 A).
*Venation pattern*.—Penniveined.
*Upperside venation coloration*.—RHS yellow green group color (near 144 C to 144 B).
*Underside venation coloration*.—RHS yellow green group color (near 144 C to 144 B).

Terminal leaflet:
*Length/width ratio*.—Longer than broad.
*Length*.—About 9.5 cm to10.0 cm.
*Width*.—About 6.0 cm to 6.5 cm.
*Cross section*.—Concave.
*Upperside*.—RHS green group (near 141 B to 141 A).
*Underside*.—RHS green group color (near 143 B to 143 A).
*Shape of leaflet*.—Ovate.
*Shape of tip*.—Acuminate.
*Shape of base*.—Acute to rounded.
*Shape of margin*.—Bi-serrate.
*Upperside rugosity*.—Medium.
*Underside texture*.—Medium.
*Venation pattern*.—Penniveined.
*Upperside venation coloration*.—RHS yellow green group color (near 144 C to 144 B).
*Underside venation coloration*.—RHS yellow green group color (near 144 C to 144 B).

Rachis:
*Length between the terminal leaflet and adjacent lateral leaflet*.—About 1.7 cm to 1.9 cm.
*Coloration*.—RHS yellow green group color (near 144 C to 144 B).

Petiole:
*Color*.—RHS yellow green group color (near 144 C to 144 B).
*Length*.—About 5.0 to 5.5 cm.
*Length* (*rachis with petiolule*).—About 6.7 cm to 7.4 cm.
*Diameter*.—About 1.5 mm to 2.0 mm in the Petiolule and about 1.0 mm to 1.5 mm in the rachis.
*Spines*.—Very few.
*Petiole texture*.—Smooth.

Stipule:
*Quantity per leaf*.—2.
*Shape*.—Lanceolate and erect.
*Length*.—About 7.0 mm to 9.0 mm.
*Width*.—Narrow. About 0.7 mm to 0.9 mm.
*Color* (*both surfaces*).—RHS green group color (near 143 C to 143 B).

Peduncle:
*Length*.—About 3.5 cm to 4.5 cm.
*Diameter*.—About 1.0 mm to 2.0 mm.
*Surface texture*.—Smooth.
*Density of spines*.—Very sparse.
*Color*.—RHS green group color (near 139 C to 139 B).

Flower bud:
*Shape*.—Rounded.
*Diameter*.—About 5.0 mm to 7.0 mm.
*Color*.—RHS green group (near 143 B to 143 A).

Flower:
*Diameter*.—About 3.5 cm to 4.0 cm.
*Number of pistils per flower*.—About 120 to 130.
*Pistil length*.—About 3.0 mm to 4.0 mm.
*Ovary shape*.—Slightly reniform.
*Ovary length*.—About 1.0 mm to 1.5 mm.
*Ovary width*.—About 0.7 mm to 0.9 mm.
*Ovary color*.—RHS green group color (near 142 D to 142 C).
*Style length*.—About 2.0 mm to 2.5 mm.
*Style color*.—RHS green-white group color (near 157 D to 157 C).
*Number of stamens per flower*.—About 100 to 110.
*Stamen length*.—About 4.5 mm to 5.5 mm.

*Stamen shape*.—Cylindrical lengthened.
*Stamen color*.—RHS yellow green group color (near 149 D).
*Pollen amount*.—Moderate to abundant.
*Pollen color*.—RHS greyed-orange group color (near 175 C to 175 B).

Petal:
*Number of petals per flower*.—About 5 to 6.
*Shape*.—Medium long flat elliptic.
*Length*.—About 1.8 cm to 2.0 cm.
*Width*.—About 0.9 cm to 1.1 cm.
*Apex shape*.—Rounded.
*Base shape*.—Narrow.
*Margin*.—Slightly uneven.
*Texture*.—Smooth.
*Color* (*both surfaces*).—RHS white group color (near 155 B to 155 A) with reddish pigmentation RHS red group (near 55 D to 55 C).

Sepal:
*Number of sepals per flower*.—About 5 to 6.
*Shape*.—Triangular shape.
*Length*.—About 6.0 mm to 9.0 mm.
*Width*.—About 3.0 mm to 4.0 mm.
*Apex shape*.—Acuminate.
*Base shape*.—Large at the base forming the calyx.
*Margin*.—Smooth and regular.
*Texture*.—Smooth.
*Color*.—RHS green group color (near 143 C to 143 A).

Fruit:
*Shape*.—Oblong.
*Length*.—About 3.7 cm to 4.3 cm.
*Width*.—About 2.7 cm to 3.1 cm.
*Color*.—RHS black group near 202 A.
*Number of drupelets per fruit*.—About 115 to 125.
*Size of single drupelet*.—About 3.0 mm to 5.0 mm.
*Drupelet arrangement around the berry*.—Slightly irregular.
*Glossiness*.—Strong.
*Firmness*.—Medium.

Seed:
*Number of seeds per drupelet*.—1.
*Shape*.—Slightly reniform.
*Color*.—RHS greyed-orange group (near 164 B to 164 A).
*Surface texture*.—Wrinkled.

Fruit bearing type: Both on previous year's cane in autumn and current year's cane in spring.

Fruiting lateral cane:
*Number of fruit per fruiting lateral cane*.—About 8 to 10 fruits.
*Average number of fruit per node*.—1 fruit.

Disease resistance: No particular sensitivity to any disease or pest has been observed for 'Plablack 1401'.

Use/market: The berries of 'Plablack 1401' are suitable for consumption as fresh fruit. Also, they are amenable to processing.

Storage qualities: 'Plablack 1401' fruits maintain their quality characteristics when keeping them in a frigo chamber at temperatures of about 2° C. during 48 hours. The fruit's color remains substantially the same. Shelf-life of 'Plablack 1401' is medium.

Planting date: Each year, about June 15 in Cartaya (Huelva), Spain, about 7° W, 37° N, 45 feet elevation.

Fall production in the same year:
10% *Flowering* (*based on June* 15 *planting date*).—About September 1.
*Time of flowers* (50% *of plants at first flower*) (*based on June* 15 *planting date*).—About September 15.
*First mature fruits* (*based on June* 15 *planting date*) .—About September 25.
*Maturity* (15-20 *g/plant*) (*based on June* 15 *planting date*).—About October 7.

Spring production in the ensuing year:
10% *Flowering* (*based on June* 15 *planting date*).—About March 25.
*Time of flowers* (50% *of plants at first flower*) (*based on June* 15 *planting date*).—About April 10.
*First mature fruits* (*based on June* 15 *planting date*) .—About April 26.
*Maturity* (15-20 *g/plant*) (*based on June* 15 *planting date*).—About May 5.

I claim:

1. A new and distinct blackberry plant of the variety substantially as shown and described.

* * * * *